United States Patent [19]

Shiue et al.

[11] Patent Number: 4,871,527
[45] Date of Patent: Oct. 3, 1989

[54] NO-CARRIER-ADDED [$^{18}$F]-N-FLUOROALKYLSPIROPERIDOLS

[75] Inventors: Chyng-Yann Shiue, East Setauket; Alfred P. Wolf, Setauket; Lan-Qin Bai; Ren-Tui Teng, both of Upton, all of N.Y.

[73] Assignee: The United States of America as represented by the United States Department of Energy, Washington, D.C.

[21] Appl. No.: 43,824

[22] Filed: Apr. 29, 1987

[51] Int. Cl.$^4$ .................... A61K 49/02; C07D 471/10
[52] U.S. Cl. ........................................ 424/1.1; 546/20
[58] Field of Search ............................ 424/1.1; 546/20

[56] References Cited
U.S. PATENT DOCUMENTS 4,656,280 4/1987 Garlick .................... 424/1.1 X

OTHER PUBLICATIONS

Welch, Michael J. et al., "Biodistribution of Derivatives of Spiroperidols", Nucl. Med. Biol., 2/2/1986, 13(5), 523-6, [Chem. Absts. 106:134386w].
Satyamurthy, Nagichettiar et al, "NCA 3-(2-Fluoroethyl)Spiperone", Nucl. Med. Biol., 2/6/1986, 13(6), 617, 620-21, 623-626-27, [Chem. Absts. 106:134389z].

Primary Examiner—John S. Maples
Attorney, Agent, or Firm—Margaret C. Bogosian; James W. Weinberger; Judson R. Hightower

[57] ABSTRACT

There is disclosed radioligands labeled with the position emitting radionuclide [$^{18}$F] suitable for dynamic study in living humans with position emission transaxial tomography. These new [$^{18}$F]-N-fluoroalkylspiroperidols, wherein the alkyl group contains from 2-6 carbon atoms, exhibit extremely high affinity for the dopamine receptors and provide enhanced uptake and retention in the brain concomitant with reduced radiation burden. These characteristics all combine to make these new radioligands useful for mapping dopamine receptors in normal and disease states in the living brain. Additionally, a new synthetic procedure for these radioligands as well as a new procedure for preparing the radiolabeled alkyl halide alkylating reagents are also disclosed.

4 Claims, 1 Drawing Sheet

NO-CARRIER-ADDED [$^{18}$F]-N-FLUOROALKYLSPIROPERIDOLS

The U.S. Government has rights in this invention pursuant to Contract Number DE-AC02-76CH00016, between the U.S. Department of Energy and Associated Universities Inc.

BACKGROUND OF THE INVENTION

The present invention is directed to the synthesis of a series of radioligands, labeled with a positron emitting radionuclide, fluorine-18, which are suitable for dynamic studies in humans using positron emission transaxial tomography. One of the preferred radio-labeled ligands of this series, no-carrier-added (NCA) N-(3-[$^{18}$F]fluoropropyl)spiroperidol exhibits extremely high affinity for dopamine receptors and provides enhanced uptake and retention in the brain concomitant with reduced radiation burden. These characteristics all combine to make NCA N-(3-[$^{18}$F]fluoropropyl)-spiroperidol a radioligand that is well suited for use in mapping dopamine receptors in normal and diseased states in the living brain.

Recent advances in the study of neuropsychiatric diseases link manifestations of a disease to chemical changes in the brain. For example, the dopamine neurotransmitter has been linked with both Parkinson's disease and schizophrenia as a source for altered synaptic transmission at the biochemical level.

The development of positron emission transaxial tomography (PET) has now made it possible to study the dopamine receptors in a living human brain. Radioligands labeled with positron emitting radionuclides permit quantitative studies based on annihilation radiation produced during positron emission. The technique consists of intravenous injection of a radioligand or radiopharmaceutical and subsequent imaging of the distribution of the radioactive label based on detection of the annihilation radiation produced during positron emission.

Radioligands which have proved useful for such studies are those with a high in vivo affinity for the dopamine receptors. To date, one of the most promising such radioligand has been [$^{18}$F]-N-methylspiroperidol whose synthesis and use is described by Shiue, et al., *Journal of Nuclear Medicine*, 27: 226–234 (1986) Arnett et al., *Life Science*, 36: 1359–1366 (1985); and Arnett et al., *Journal of Nuclear Medicine*, 27: 1878–1882 (1986). However, there are several significant drawbacks to the use of this radioligand. The synthesis of [$^{18}$F]-N-methylspiroperidol is a multi-step process, the yields are not optimum, and the starting materials used to prepare this tracer, namely cyclopropyl-p-nitrophenyl ketone and 3-methyl-1-phenyl-1,3,8-triazaspiro[4.5]deca-4-one, are not commercially available materials and thus have to be synthesized independently prior to synthesis of the radioligand.

In the present invention, no-carrier-added (NCA) N-(3-[$^{18}$F]fluoropropyl)spiroperidol, a new radioligand which exhibits similar uptake into the brain's dopamine receptor rich areas as [$^{18}$F]-N-methylspiroperidol and is thus equally valuable in studying dopamine receptors in humans using PET is prepared by the N-alkylation of spiroperidol. Both spiroperidol and the alkylating agent precursor prior to [$^{18}$F]*labeling are commercially available materials thus greatly simplifying the synthesis of the valuable radioligand and yielding the tracer in radiochemical yields greater than* 20% at high specific activity. The biodistribution and kinetic distribution of N-(3-[$^{18}$F]fluoropropyl)spiroperidol are appropriate for mapping dopamine receptors and the striatal accumulation of radioactivity was blocked stereoselectively by (+)-butaclamol. The baboon blood total plasma radioactivity clearance was rapid and the analysis of the metabolic stability of this novel radioligand in mouse brain for one hour indicated that it is very stable to metabolic transformation in the central nervous system. N-(3-[$^{18}$F]fluoropropyl)-spiroperidol has the characteristics to be a useful radioligand for PET studies of the dopamine receptors in humans.

In a further aspect of the present invention, a series of [$^{18}$F]-N-fluoroalkylspiroperidols similar to N-(3-[$^{18}$F]fluoropropyl)spiroperidol are prepared for use in PET studies.

In a still further aspect of the present invention, [$^{18}$F]fluoroalkyl halides are prepared and used in the synthesis of the novel [$^{18}$F]-N-fluoroalkylspiroperidols.

Utility Statement

The compounds of this invention, NCA [$^{18}$F]-N-fluoroalkylspiroperidols, with NCA N-(3-[$^{18}$F]fluoropropyl)spiroperidol being preferred, are positron emitting radiopharmaceuticals or radioligands suitable for mapping dopamine receptors in normal and disease states in the living brain with positron emission transaxial tomography (PET), a noninvasive imaging method for use in medical diagnosis and biological investigations.

DETAILED DESCRIPTION OF THE INVENTION

Figure 1:
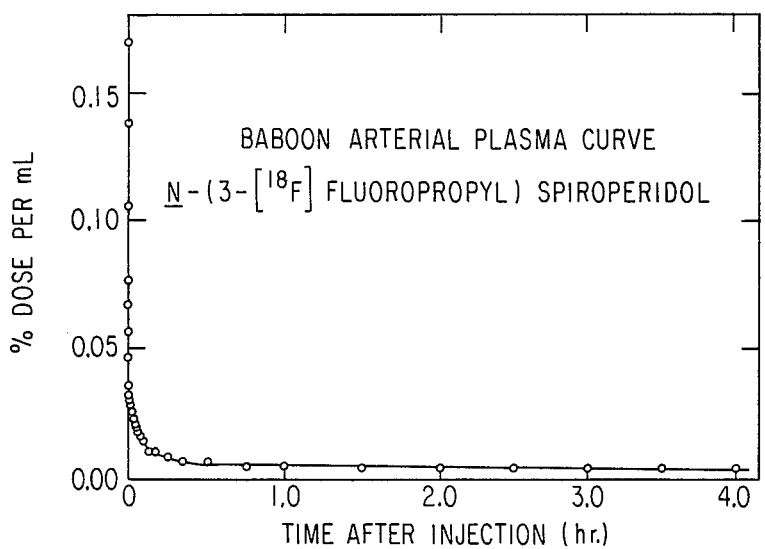
FIG. 1 Baboon blood total plasma radioactivity clearance curve following injection of N-(3-[$^{18}$F]fluoropropylspiroperidol.

The present invention is directed to a new series of compounds, no-carrier-added [$^{18}$]-*labeled N-fluorospiroalkyl where the alkyl group contains from* 2 to 6 carbon atoms. Examples of the compounds of the present invention are NCA N-(2-[$^{18}$F]fluoroethyl)spiroperidol, NCA N-(3-[$^{18}$F]fluoropropyl)spiroperidol and NCA N-(3-[$^{18}$F]fluorobutyl)spiroperidol with NCA N-(3-[$^{18}$F]fluoropropyl)spiroperidol being the preferred compound in this series. These new NCA$^{18}$F-labeled N-fluoroalkylspiroperidols are synthesized by N-alkylation of spiroperidol with the appropriate NCA $^{18}$F-labeled alkyl halides. Suitable alkyl halides for this purpose include 1-halo-2-[$^{18}$F]fluoroethane and 1-halo-3-[$^{18}$F]fluoropropane. In the case of the NCA [18F]fluoroalkyl halides used as N-alkylating agents in this process, suitable halides include bromides, chlorides and iodides.

A further aspect of the present invention is a new process for synthesizing the NCA [$^{18}$F]fluoroalkyl halides used as N-alkylating agents in the synthesis of the new and valuable NCA [$^{18}$F]fluoroalkylspiroperidols. These NCA [$^{18}$F]fluoroalkyl halides are prepared by nucleophilic aliphatic substitution of alkyl halides with NCA [$^{18}$F]fluoride. Radiofluorination of alkyl halides of the formula $(CH_2)_nX_2$ wherein X is a halogen selected from the group consisting of chlorine, bromine and iodine and n is 2 to 6 is accomplished by reacting said alkyl halides with NCA [$^{18}$F]*fluoride, preferably as the potassium salt suspended in a cryptate such as Kryptofix 2.2.2*. The reaction is conducted in an organic solvent such as MeCN or DMSO and yields the corresponding NCA [$^{18}$F]fluoroalkyl halide. The radiofluorination can be conducted at a temperature in the range of 50° C. to 150° C., with the choice of temperature dependent upon the choice of solvent system.

EXAMPLE 1

Materials and Methods

Acetonitrile is an HPLC grade reagent from Fischer Scientific Co. Kryptofix 2.2.2 was purchased from MCB Chemical Co. 1,3-Dibromopropane and 1,3-diiodopropane were purchased from Eastman Kodak Co. and used without further purification. 1,2-Dibromoethane and 1,2-diiodoethane were purchased from Fischer Scientific Co. and Aldrich Chemical Co. respectively. 1-Bromo-2-fluoroethane was purchased from Fairfield Chemical Co. 1-Bromo-3-fluoropropane was synthesized by a known method [Feliu et al., *Res. Comm. Chem. Pathol. Pharmacol.*, 49, 323–336 (1985)]. Tetrabutylammonium hydroxide (0.4M in H$_2$O) was purchased from Eastman Kodak Co.

Thin-layer chromatographic analyses (TLC) were performed on plastic-backed TLC plates (Merck) with CH$_2$Cl$_2$:CH$_3$OH (9:1) as solvent. HPLC analyses were carried out with a Perkin-Elmer Series 2 or 3B liquid chromatograph equipped with a radioactivity monitor (Berthold Model LB503). An analytical reversed-phase C18 column (4.5×250 mm) was used with either CH$_3$OH:H$_2$O:(i-Pr)$_2$NH (70:30:0.1) or CH$_3$OH:0.02N NH$_4$CO$_2$H (75:25) as the solvent with a flow rate of 1.5 ml/min. For the preparative separation a semi-preparative C18 column (10×250 mm, Phenomenex, (ODS-1) was used with CH$_3$OH:H$_2$O:(iPr)$_2$NH (70:30:0.1) as the solvent with a flow rate of 4 ml/min. The C18 Sep-Pak cartridges were obtained from Waters Associates.

EXAMPLE 2

A General Synthesis of NCA 1-[$^{18}$F]Fluoroalkyl Halides by Nucleophilic Aliphatic Substitution of Alkyl Halides with NCA [$^{18}$F]Fluoride No-carrier-added aqueous[$^{18}$F]fluoride (approx. 1 ml) prepared by the $^{18}$O(p,n)$^{18}$F reaction [Ruth et al., *Radiochim. Acta.*, 26: 21 (1978)], on a small volume enriched water (95–99% $^{18}$O) target [Wieland et al., *Journal of Nuclear Medicine*, 24, 122 (1983)] was added to a solution of 10 mg (26.6 μmol) of Kryptofix 2.2.2 and 2.5 mg (18 μmol) of K$_2$CO$_3$ in 0.2 ml of CH$_3$CN in an open Pyrex vessel. The water was removed using a stream of nitrogen at 115° C. and coevaporated to dryness with CH$_3$CH (3×0.5 ml). To the dried K[$^{18}$F] was added 23 μmol of alkyl halide in 0.5 ml of CH$_3$CN and the vessel was covered. This solution was heated at 75° C. for 10 min, cooled to room temperature and then 3 ml of water was added. The mixture was transferred onto a C18 Sep-Pak cartridge which had been prewashed with 3 ml of CH$_3$OH followed by 4 ml of water. The Sep-Park cartridge was washed with 4 ml of water and the washing was discarded. The product, NCA 1-[$^{18}$F]fluoroalkyl halide, was eluted with 5 ml of pentane which was filtered through an anhydrous K$_2$CO$_3$ tube. The identities of the products were confirmed by comparison of their HPLC retention times with authentic samples. The results are listed in Table 1.

TABLE 1

Radiochemical yield of NCA $^{18}$F—labeled fluoroalkyl halides from the nucleophilic aliphatic substitution of alkyl halides with NCA [$^{18}$F]fluoride in CH$_3$CN at 65–75° C.[a]

| | Radiochemical Yield (%)[b] $^{18}$F(CH$_2$)$_n$X | |
|---|---|---|
| (CH$_2$)$_n$X$_2$ | With Kryptofix 2.2.2 | Without Kryptofix 2.2.2 |
| a; n = 2, X = I | 5 | — |
| b; n = 2, X = Br | 30–40 | — |
| c; n = 3, X = I | 30–40 | <5 |
| d; n = 3, X = Br | 30–40 | — |

[a]Reaction time = 10–15 min; Substrate Concentration: ca. 20 μmole, K[$^{18}$F] (NCA); pyrex vessel.
[b]Products were isolated by C18 Sep Pak cartridges extraction (H$_2$O/pentane) and were identified using a radio HPLC [Perkin-Elmer Series 2 or 3B Liquid Chromatograph equipped with a UV detector and connected to a Berthold Model LB 503 radioactivity detector. C18 column with MeOH:H$_2$O:(i-Pr)$_2$NH (70:30:0.1) as elution solvent] and comparison of retention times with those of authentic samples. The yield has been decay corrected.

EXAMPLE 3

Optimization of $^{18}$F Substitution in the Alkyl Halides

K[$^{18}$F] was prepared as described in Example 2 and the yield of the substitution reaction was measured by carrying out the reaction as described in Example 2. The identities of the products were confirmed by comparison of their HPLC retention times with authentic samples. Variables were solvent, substrate, substrate concentration and reaction temperature. Table 2 sets forth the results measuring the effect of solvent and reaction temperature on yield of 1-[$^{18}$F]-fluoro-3iodopropane. Table 3 sets forth the results measuring the effect of substrate concentration on yield of the [$^{18}$F]fluoroalkyl halides.

TABLE 2

Effects of Solvent and Temperature on Yield of 1-[$^{18}$F]Fluoro-3-Iodopropane from (CH$_2$)$_3$I$_2$[a]

| Run | Solvent | Temperature (°C.) | Yield(%)[b] |
|---|---|---|---|
| 1 | CH$_3$CN | 70 | 33 |
| 2 | CH$_3$CN | 75 | 45 |
| 3 | CH$_3$CN | 80 | 35 |
| 4 | CH$_3$CN | 90 | 43 |
| 5 | DMSO | 70 | 6 |
| 6 | DMSO | 80 | 4 |
| 7 | DMSO | 90 | 4 |
| 8 | DMSO | 100 | 3 |
| 9 | DMSO | 120 | 2 |
| 10 | DMSO | 140 | 2 |

[a]Reactions were carried out in a Pyrex vessel.
[b]The yield has been decay corrected.

TABLE 3

The Influence of Substrate and Substrate Concentration on Yield of 1-[$^{18}$F]Fluoropropyl Halides[a]

| Substrate | Substrate Concentration (μm) | Yield(%)[b] |
|---|---|---|
| (CH$_2$)$_3$Br$_2$ | 4.5 | 28 |
| (CH$_2$)$_3$Br$_2$ | 24.8 | 36 |
| (CH$_2$)$_3$Br$_2$ | 45 | 28 |
| (CH$_2$)$_3$I$_2$ | 4.5 | 25 |
| (CH$_2$)$_3$I$_2$ | 25 | 24 |
| (CH$_2$)$_3$I$_2$ | 45 | 28 |

[a]All reactions were carried out at 75° C. in a Pyrex vessel.
[b]Percentage of activity isolated in the product, corrected for decay.

EXAMPLE 4

Synthesis of NCA N-(2-[$^{18}$F]Fluoroethyl)spiroperidol

To the dried K[$^{18}$F] as described in Example 2 was added 10 mg (53.2 μmol) of 1,2-dibromoethane in 0.5 ml of CH$_3$CN and the vessel was covered. The solution was heated at 65° C. for 10 min, cooled to room temperature followed by the addition of 1 ml of water. The product, 1-bromo-2-[$^{18}$F]fluoroethane was removed with a slow stream of nitrogen. The nitrogen stream was passed into a V-shaped vessel containing 4.1 mg (10.4 μmol) of spiroperidol and 40 μl (16 μmol) of tetrabutylammonium hydroxide in 0.2 ml of DMF at ice-bath temperature. The vessel was set up in an ionization chamber to monitor the activity of 1-bromo-2-[$^{18}$F]fluoroethane. As soon as no more activity entered the reaction vessel, the bubbling procedure was stopped and the reaction vessel was kept at 80° C. for 15 min. The crude product was dissolved in 1.5 ml of HPLC solvent for preparative HPLC purification. Preparative HPLC purification of the crude product was accomplished using a 10×250 mm reversed-phase column (Phenomenex, ODS-1) using CH$_3$OH:H$_2$O:(i-Pr)$_2$NH (70:30:0.1) with a flow rate of 4 ml/min. Retention times for spiroperidol and N-(2-[$^{18}$F]fluoroethyl)spiroperidol were 14 and 19 min respectively using this system. The effluent of the HPLC column is passed through a UV detector at 254 nm and into a fraction collector set up in an ionization chamber. The product fraction was taken from 19-22 minutes after injection, at which time the UV trace had returned to base line. The HPLC eluate was evaporated, the residue coevaporated with 5 ml of ethanol, and finally coevaporated with 1 ml of 2% HCl-ethanol to dryness. A stream of dry N$_2$ was passed over the residue for about 1 minute to remove remaining traces of solvent. To the residue was added 3 ml of saline and the resulting solution was filtered through a 0.22 μm millipore filter into a multi-injection vial. The radiochemical yield of NCA N-(2-[$^{18}$F]fluoroethyl)-spiroperidol synthesized by this method was approx. 2% (EOB) (based on total [$^{18}$F]fluoride delivered from the target) in a synthesis time of approx. 70 min from EOB.

EXAMPLE 5

Synthesis of NCA N-(3-[$^{18}$F]fluoropropyl)spiroperidol

NCA N-(3-[$^{18}$F]fluoropropyl)spiroperidol was synthesized from two different substrates.

Method A: Spiroperidol (5 mg) and tetrabutylammonium hydroxide (0.4M in H$_2$O, 40 μl) were added to NCA 1-[$^{18}$F]fluoro-3-iodopropane in 5 ml of pentane in an open test tube. An oil bath (110° C.) was applied and when the volume of the pentane solution was reduced to 0.2 ml, 0.5 ml of a 1:10 solution of DMF-THF was added and the mixture was heated for 10 min after THF had evaporated. The product was purified as described in Example 4. Retention times for spiroperidol, NCA N-(3-[$^{18}$F]fluoropropyl)spiroperidol and the by-product N-(3-iodopropyl)spiroperidol were 14, 20 and 24 minutes respectively using this system. The radiochemical yield of NCA N-(3-[$^{18}$F]fluoropropyl)spiroperidol synthesized by this method was approx. 20% (EOB) (based on total [$^{18}$F]fluoride delivered from the target) in a synthesis time of approx. 70 min from EOB. The total mass of the product was 2-5 nmol as determined by the UV absorbance of the radioactive peak as compared to a standard solution of N-(3-fluoropropyl)spiroperidol.

Method B: To the dried K[$^{18}$F] prepared as described in Example 2 was added a solution of 1,3-dibromopropane (6.8 mg) in 0.5 ml of CH$_3$CN. The solution was heated at 65° C. for 10 min and the procedure described in Example 2 was followed to obtain a solution of 1-bromo-3-[$^{18}$F]fluoropropane in pentane. The alkylation step was carried out using spiroperidol (5 mg) and tetrabutylammonium hydroxide (40 μl) as described in Example 4 except that the reaction temperature was 85°-100° C. In this synthesis, N-(3-bromopropyl)-spiroperidol is also produced as a by-product but was well separated using the HPLC system. The radiochemical yield of NCA N-(3-[$^{18}$F]fluoropropyl)spiroperidol synthesized y this method was 1% (EOB) (based on total [$^{18}$F]fluoride delivered from the target) in a synthesis time of 70 min from EOB.

EXAMPLE 6

Tissue Distribution of NCA N-(3-[$^{18}$F]fluoropropyl)spiroperidol in Mice

Female albino mice (BNL strain), 22-27 g, were injected in a lateral tail vein with 24-85 μCi of N-(3-[$^{18}$F]fluoropropyl)spiroperidol in 100 μl of isotonic saline solution. To demonstrate specific localization each mouse was pretreated with 2 mg/kg, i.v. of either (−)-butaclamol (control) or (+)-butaclamol (to block stereospecific binding sites) 45-55 minutes before injection of the radioligand.

TABLE 4

Tissue Distribution of N-(3-[$^{18}$F]Fluoropropyl)sprioperidol in Mice (n = 1-4)

| | | \multicolumn{6}{c|}{Time After Injection} | | | | | |
|---|---|---|---|---|---|---|---|---|---|
| | | 5 Min | | | | 60 Min | | | 120 Min | |
| Organ | Pre-treatment* | %/gram | | %/organ | | %/gram | | %/organ | %/gram | | %/organ |
| Striatum | − | 3.4 | (3.2–3.7) | 0.084 | (0.068–0.099) | 4.1 | (3.2–4.7) | 0.089 (0.064–0.142) | 4.3 | (4.0–4.7) | 0.14 (0.11–0.17) |
| | + | 1.6 | 1.2–2.1 | 0.051 | (0.037–0.065) | 0.51 | (0.39–0.60) | 0.013 (0.009–0.018) | 0.36 | | 0.010 |
| Cerebellum | − | 3.4 | (2.0–7.1) | 0.24 | (0.13–0.45) | 0.55 | (0.48–0.64) | 0.040 (0.032–0.048) | 0.42 | (0.33–0.52) | 0.028 (0.023–0.032) |
| | + | 1.6 | (1.2–2.0) | 0.11 | (0.08–0.14) | 0.27 | (0.20–0.35) | 0.019 (0.013–0.025) | | 0.15 | 0.012 |
| Whole Brain | − | 2.7 | (2.3–3.2) | 1.1 | (0.9–1.4) | 1.6 | (1.4–1.8) | 0.67 (0.59–0.77) | 1.2 | (1.0–1.5) | 0.56 (0.44–0.63) |
| | + | 1.8 | (1.3–2.2) | 0.79 | (0.57–1.00) | 0.37 | (0.26–0.50) | 0.16 (0.11–0.23) | | 0.21 | 0.097 |
| Blood | − | 1.8 | (1.4–2.0) | | | 0.80 | (0.62–1.01) | | 0.33 | (0.26–0.43) | |
| | + | 1.7 | (1.4–2.1) | | | 0.85 | (0.66–1.17) | — | | 0.33 | — |
| Heart | − | 5.5 | (4.9–6.2) | 0.58 | (0.48–0.72) | 1.1 | (0.9–1.3) | 0.12 (0.09–0.14) | 0.44 | (0.34–0.52) | 0.045 (0.036–0.051) |
| | + | 5.3 | (3.8–6.7) | 0.58 | (0.44–0.71) | 1.2 | (0.8–1.6) | 0.14 (0.10–0.20) | | 0.46 | 0.045 |
| Lungs | − | 35 | (28–41) | 4.5 | (3.8–5.0) | 4.4 | (3.8–5.0) | 0.56 (0.48–0.61) | 1.8 | (1.5–2.0) | 0.24 (0.22–0.26) |
| | + | 28 | (24–32) | 4.1 | (2.8–5.4) | 4.2 | (3.5–5.4) | 0.69 (0.56–0.88) | | | |
| Liver | − | 16 | (9–19) | 19 | (13–22) | 6.0 | (4.7–7.2) | 7.4 (5.7–10.2) | 3.1 | (2.7–3.4) | 3.6 (3.2–4.0) |
| | + | 16 | (13–20) | 23 | (19–27) | 6.0 | (4.4–8.5) | 8.7 (6.5–12.6) | | 3.3 | 4.4 |
| Spleen | − | 10 | (6–12) | 1.3 | (0.8–1.8) | 2.9 | (2.5–3.2) | 0.38 (0.28–0.48) | 1.1 | (0.9–1.2) | 0.12 (0.09–0.16) |
| | + | 14 | (10–17) | 1.9 | (1.6–2.3) | 2.8 | (1.8–3.5) | 0.43 (0.27–0.53) | | 1.1 | 0.16 |
| Kidneys | − | 19 | (15–22) | 5.9 | (4.6–7.1) | 4.1 | (3.4–5.2) | 1.3 (1.0–1.7) | 1.9 | (1.5–2.1) | 0.61 (0.47–0.72) |
| | + | 20 | (15–25) | 7.8 | (6.5–9.1) | 4.7 | (3.8–6.6) | 1.6 (1.3–2.4) | | 2.4 | 0.79 |
| Small Intestines | − | 8.8 | (6.7–9.6) | 9.6 | (7.2–11.3) | 5.6 | (4.9–6.0) | 6.2 (4.8–7.6) | 2.5 | (1.8–3.5) | 2.6 (1.8–3.8) |
| | + | 8.8 | (7.1–10.5) | 9.3 | (8.5–10.1) | 8.3 | (4.5–14.9) | 11 (4.2–23.7) | | 4.8 | 4.4 |
| Femur | − | 3.3 | (2.2–3.8) | | | 9.1 | (8.5–10.0) | — | 9.0 | (8.1–9.9) | — |
| | + | 3.8 | (3.0–4.7) | | | 6.5 | (4.7–10.6) | — | | 8.4 | — |
| Muscle | − | 3.1 | (2.6–3.5) | | | 1.0 | (0.8–1.2) | — | 0.64 | (0.32–1.03) | — |
| | + | 3.7 | (2.6–4.7) | | | 1.3 | (0.8–1.9) | — | | 0.53 | — |

*Mice were pretreated with 2 mg/kg, i.v., of either (−)-butaclamol (−), or (+)-butaclamol (+).

The mice were killed by cervical dislocation and decapitation at 5, 60 and 120 min after injection. The dissected tissues were blotted to remove adhering blood and placed in tared counting vials. A sample of blood was obtained from the trunk immediately after decapitation. The entire tail was counted to verify the patency of the tail vein injection. All samples were counted and weighed, and the activity expressed as percent of injected dose per organ or percent of injected dose per gram of tissue. The results are listed in Table 4.

EXAMPLE 7

Metabolic Stability of N-(3-[$^{18}$F]fluoropropyl)spiroperidol in Mouse Brains

Three female albino mice (BNL strain), 27–30 g, were injected in a lateral tail vein with 100–20 μCi of N-(3-[$^{18}$F]fluoropropyl)spiroperidol in 100 μl of isotonic saline solution. At 1 hr after injection, the mice were killed by cervical dislocation. The brain was rapidly removed, homogenized either in a mixture of 2 ml of CH$_3$OH and 4 ml of 0.4M HClO$_4$, or in 2 ml of CH$_3$OH alone. The samples were centrifuged, and the CH$_3$OH fractions (or the entire supernants in the case of CH$_3$OH alone) were analyzed for unchanged N-(3-[$^{18}$F]fluoropropyl)spiroperidol [Arnett et al., *Life Sci.*, 36, 1359–1366 (1985)] and analyzed by HPLC (C18 column, 4.5×250 mm, CH$_3$OH:0.2N NH$_4$CO$_2$H (90:10), 1.5 ml/min). The results are listed in Table 5.

EXAMPLE 8

PET Baboon Studies

A young adult (11 kg) female baboon (*Papio anubis*) was anesthetized initially with ketamine and subsequently maintained under halothane/nitrous oxide anesthesia for two PETT studies as described in the Arnett et al. paper referenced in Example 7. In the first study, the animal was pretreated with 0.5 mg/kg of (−)-butaclamol, i.v., 36 min before injection of 7.4 mCi of N-(3-[$^{18}$F]fluoropropyl)spiroperidol. In the second study (one week later), the same baboon was pretreated with 0.5 mg/kg of (+)-butaclamol, i.v., 25 min before injection of 7.9 mCi of N-(3-[$^{18}$F]fluoropropyl)spiroperidol. PET scans were made continually for 4 hr from the time of radioisotope injection. Regions of interest corresponding to the striata and cerebellum were selected.

Baboon Plasma Analyses: Blood was sampled from the femoral artery at initial intervals of 5 sec. Aliquots of plasma were counted to determine the total plasma radioactivity clearance curve. Representative samples (Table 6) were also analyzed for unchanged N-(3-[$^{18}$F]fluoropropyl)spiroperidol. The total recovery of $^{18}$F applied to C-18 Sep-pak ranged from 90–103%.

EXAMPLE 9

Baboon Blood Kinetics and Metabolism

The baboon blood total plasma radioactivity clearance curve following injection of NCA N-(3-[$^{18}$F]fluoropropyl)spiroperidol is depicted in FIG. 1. The blood clearance was very rapid. The appearance of metabolites in the blood was also rapid (Table 6). At 10 min after injection 68% of plasma radioactivity was due to unchanged N-(3-[$^{18}$F]fluoropropyl)spiroperidol.

TABLE 6

| | Analysis of $^{18}$F Radioactivity in Baboon Plasma Samples* | | | | |
|---|---|---|---|---|---|
| | % Recovery of Total $^{18}$F Applied to C-18 Sep-Pak | | | % of $^{18}$F in MeOH as | % of Unchanged |
| Min After Injection | H$_2$O Eluate | NaOH Eluate | MeOH Eluate | N—(3-[$^{18}$F]fluoropropyl)spiroperidol | N—(3-[$^{18}$F])fluoropropyl)spiroperidol |
| 0.67 | 8 | 2 | 93 | 98 | 91 |
| 4.0 | 10 | 4 | 83 | 99 | 82 |
| 10 | 17 | 6 | 71 | 96 | 68 |
| 30 | 31 | 14 | 45 | 90 | 41 |
| 120 | 49 | 18 | 30 | 74 | 22 |

*Plasma samples were extracted with MeOH—0.4M HClO$_4$

EXAMPLE 10

Baboon Brain Kinetics

Figure 2:
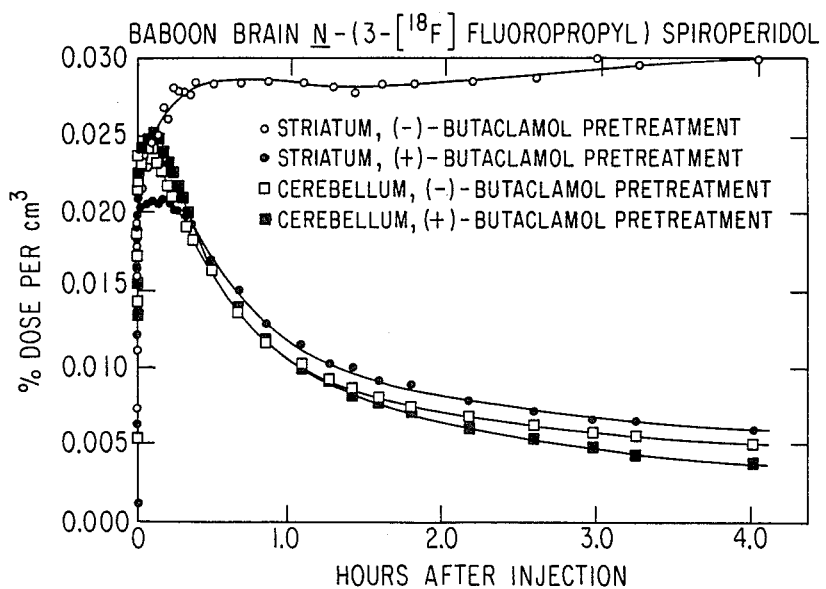
FIG. 2 shows the distribution of N-(3-[$^{18}$F]fluoropropyl)spiroperidol to striatum and cerebellum of the baboon in the control study following pretreatment with the inactive (−)-butaclamol.

FIG. 2 shows the distribution of N-(3-[$^{18}$F]fluoropropyl)spiroperidol to striatum and cerebellum of the baboon in the control study following pretreatment with the inactive (−)butaclamol. Influx of this compound into both brain regions was nearly equal for the first few minutes, but radioactivity then declined rapidly in the cerebellum, while increasing for up to 4 hrs in the striatum.

Pretreatment of the baboon with the same dose of the pharmacologically active (+)-butaclamol demonstrates stereoselective inhibition of the striatal retention of radioactivity.

TABLE 5

| | Average Metabolic Stability of N—(3-[$^{18}$F]fluoropropyl) spiroperidol in Mouse Brains 1 hr After Injection | | | | |
|---|---|---|---|---|---|
| | Percent Recovery of Total $^{18}$F Applied to C-18 Sep-Pak | | | Percent of $^{18}$F in MEOH as | Percent of Unchanged |
| Treatment | H$_2$O Eluate | NaOH Eluate | MeOH Eluate | N—(3-[$^{18}$F]fluoropropyl)-spiroperidol | N—(3-[$^{18}$F]fluoropropyl)spiroperidol |
| MeOH—HClO$_4$[a] | 4.2 | 1.3 | 73 | 94 | 69 |
| 2X MeOH—HClO$_4$[b] | 11 | 3.1 | 81 | 94 | 76 |
| MeOH Alone | — | — | 65 | 97 | 62 |

[a]The precipitates were separated without further washings.
[b]The precipitates were separated and washed with MeOH—HClO$_4$ again.

We claim:

1. No-carrier-added [$^{18}$F]-N-fluoroalkylspiroperidols wherein the alkyl group contains from 2–6 carbon atoms.

2. No-carrier-added N-(3-[$^{18}$F]fluoropropyl) spiroperidol.

3. A method of mapping dopamine receptors in normal and disease states in the living mammalian brain consisting of injecting an effective amount of a no-carrier-added [$^{18}$F]-N-fluoroalkylspiroperidol, wherein the alkyl group contains from 2–6 carbon atoms, as the radiolabeled material in a positron emission transaxial tomographic procedure.

4. The method of claim 3 wherein the radiolabeled material is positron-emitting no-carrier-added N-(3-(18F)-fluoropropyl)spiroperidol.

* * * * *